United States Patent
Cook et al.

(10) Patent No.: US 12,059,485 B2
(45) Date of Patent: Aug. 13, 2024

(54) PERSONAL CLEANSING COMPOSITIONS COMPRISING A SURFACTANT SYSTEM CONSISTING OF AN ALKYL ETHER SULFATE AND BETAINE

(71) Applicant: Conopco, Inc., Englewood Cliffs, NJ (US)

(72) Inventors: Joanne Louise Cook, Wirral (GB);
Claire Louise Jones, Wirral (GB);
Smita Puntambekar, Wirral (GB);
Robert George Riley, Wirral (GB);
Pierre Starck, Wirral (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 626 days.

(21) Appl. No.: 17/056,685

(22) PCT Filed: Jun. 12, 2019

(86) PCT No.: PCT/EP2019/065407
§ 371 (c)(1),
(2) Date: Nov. 18, 2020

(87) PCT Pub. No.: WO2019/243143
PCT Pub. Date: Dec. 26, 2019

(65) Prior Publication Data
US 2021/0251857 A1 Aug. 19, 2021

(30) Foreign Application Priority Data
Jun. 21, 2018 (EP) .................................... 18179144

(51) Int. Cl.
*C11D 1/29* (2006.01)
*A61K 8/06* (2006.01)
(Continued)

(52) U.S. Cl.
CPC ............... *A61K 8/062* (2013.01); *A61K 8/20* (2013.01); *A61K 8/368* (2013.01); *A61K 8/442* (2013.01);
(Continued)

(58) Field of Classification Search
CPC .... C11D 1/29; C11D 1/90; C11D 1/94; C11D 3/0094; C11D 3/373; C11D 9/10; C11D 9/36; C11D 17/0021; C11D 2111/12
See application file for complete search history.

(56) References Cited

U.S. PATENT DOCUMENTS 5,990,059 A    11/1999  Finel et al.
6,004,915 A *  12/1999  Elliott ...................... C11D 1/94
                                                    510/427
(Continued)

FOREIGN PATENT DOCUMENTS

CN     108024936     5/2018
DE     102011085610  5/2013
(Continued)

OTHER PUBLICATIONS

Search Report and Written Opinion in EP18179144; Dec. 3, 2018.
(Continued)

*Primary Examiner* — Charles I Boyer
(74) *Attorney, Agent, or Firm* — Foley & Lardner LLP

(57) ABSTRACT

A personal cleansing comprising, in an aqueous continuous phase: a total amount of anionic surfactant, amphoteric surfactant and zwitterionic surfactant consisting of: (i) from 3 wt % to less than 7 wt %, by weight of the total composition at 100% activity, of an alkyl ether sulfate anionic surfactant of general formula (I): $R—O—(CH_2CH_2—O)_n—SO_3-M+$ in which R is selected from linear or branched alkyl groups having from 10 to 14 carbon atoms and mixtures thereof; n is a number that represents the average degree of ethoxylation and ranges from 1.5 to 2.5; and M is a solubilizing cation; (ii) a betaine surfactant selected from an amido betaine amphoteric surfactant of general formula (II): where m is 2 or 3; $R^1C(O)$ is selected from linear or branched, saturated or unsaturated acyl groups having from 8 to 22 carbon atoms and mixtures thereof; and $R^2$ and $R^3$ are each independently selected from alkyl, hydroxyalkyl or carboxyalkyl groups having from 1 to 6 carbon atoms and mixtures thereof; an alkyl betaine of general formula (III): wherein R is a coco chain, and mixtures thereof; and (iii) one or more dispersed benefit agents selected from emulsified silicones with a mean diameter (D3,2) of 4 micrometres or less; in which the weight ratio of (i) to (ii) ranges from 1 to 1 to 4.5:1 and the pH of the composition is from 3 to 6.5, and the combined amount of (i) and (ii) ranges from 5 wt % to 9 wt % (by weight based on the total weight of the composition); gives mildness benefit without compromising on cleaning and rheology; and wherein the composition further comprises an inorganic electrolyte.

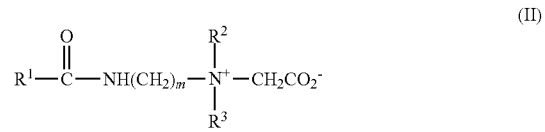

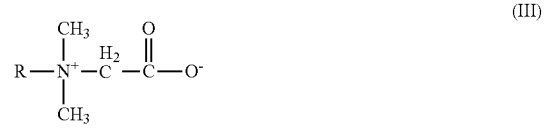

18 Claims, No Drawings

(51) Int. Cl.
  *A61K 8/20* (2006.01)
  *A61K 8/368* (2006.01)
  *A61K 8/44* (2006.01)
  *A61K 8/46* (2006.01)
  *A61K 8/73* (2006.01)
  *A61K 8/81* (2006.01)
  *A61K 8/891* (2006.01)
  *A61Q 5/12* (2006.01)
  *A61Q 19/10* (2006.01)

(52) U.S. Cl.
  CPC .............. *A61K 8/463* (2013.01); *A61K 8/737* (2013.01); *A61K 8/8147* (2013.01); *A61K 8/891* (2013.01); *A61Q 5/12* (2013.01); *A61Q 19/10* (2013.01)

(56) References Cited

U.S. PATENT DOCUMENTS

| | | | |
|---|---|---|---|
| 6,194,363 B1* | 2/2001 | Murray | A61Q 5/12 424/70.13 |
| 6,475,474 B1* | 11/2002 | Ricca | A61Q 19/00 424/59 |
| 6,844,309 B1* | 1/2005 | Sivik | C07D 309/12 510/421 |
| 2004/0146475 A1* | 7/2004 | Peffly | A61K 8/463 424/70.13 |
| 2004/0157984 A1 | 8/2004 | Sakai et al. | |
| 2005/0191265 A1 | 9/2005 | Seigneurin et al. | |
| 2005/0276778 A1* | 12/2005 | Chen | A61Q 19/00 424/70.16 |
| 2006/0024256 A1 | 2/2006 | Wells et al. | |
| 2006/0024381 A1 | 2/2006 | Gamble | |
| 2009/0197791 A1 | 8/2009 | Balastre et al. | |
| 2012/0009285 A1* | 1/2012 | Wei | A61K 8/922 514/552 |
| 2012/0076747 A1* | 3/2012 | Bierganns | C11D 1/345 424/70.13 |
| 2013/0150338 A1* | 6/2013 | Ananthapadmanabhan | A61K 8/27 514/188 |
| 2014/0154200 A1 | 6/2014 | Lizarraga | |
| 2014/0348927 A1* | 11/2014 | Schroeder | A61K 8/73 510/122 |
| 2018/0110704 A1* | 4/2018 | Zhao | A61K 8/494 |
| 2018/0256470 A1 | 9/2018 | Ainger | |
| 2018/0344612 A1* | 12/2018 | Zhao | A61K 8/89 |
| 2019/0178774 A1* | 6/2019 | Wei | A61K 8/37 |

FOREIGN PATENT DOCUMENTS

| | | |
|---|---|---|
| EP | 0468721 | 1/1992 |
| EP | 0529883 | 3/1993 |
| EP | 1433464 | 6/2004 |
| JP | 2008214263 | 9/2008 |
| JP | 2013544226 | 12/2013 |
| WO | WO9739089 | 10/1997 |
| WO | WO1998005296 | 2/1998 |
| WO | WO1998031327 | 7/1998 |
| WO | WO9929286 A1 | 6/1999 |
| WO | WO9953889 | 10/1999 |
| WO | WO2012074943 | 6/2012 |
| WO | WO2012072424 | 12/2012 |
| WO | WO2015117757 | 8/2015 |
| WO | WO2017063806 | 4/2017 |
| WO | WO2017097817 | 6/2017 |

OTHER PUBLICATIONS

Search Report and Written Opinion for PCTEP2019065407; Sep. 4, 2019.
Notice of Opposition in EP19729071 (3773457); Jul. 13, 2022; European Patent Office (EPO).
Huntsman; Empicol* ESB3/M; Safety Data Sheet; 2000; pp. 1-4.
Rhodia; Mirataine BET C-30; Product Data Sheet N000751; Feb. 2008; pp. 1.
Online-Enzyklopadie Wikipedia; Natriumdodecylpoly(oxyethylen)sulfat; 2018; pp. 1-3, with machine translation; Germany.

* cited by examiner

PERSONAL CLEANSING COMPOSITIONS COMPRISING A SURFACTANT SYSTEM CONSISTING OF AN ALKYL ETHER SULFATE AND BETAINE

The present application is a U.S. national stage application under 35 U.S.C. § 371 of International Application No. PCT/EP2019/065407, filed Jun. 12, 2019, which in turn claims the benefit of European Patent Application No. 18179144.3, filed Jun. 21, 2018, the content of each of which is incorporated herein by reference in its entirety.

FIELD OF THE INVENTION

The present invention relates to personal cleansing compositions such as liquid soaps, body washes and shampoos.

BACKGROUND AND PRIOR ART

Alkyl sulfates and alkyl ether sulfates, for example, sodium laureth ether sulphate (SLES), are typically used as primary surfactants in personal cleansing compositions. Higher contents of such surfactants lead to improved cleaning benefit but increased irritation potential. Cocamidopropyl betaine (CAPB) is typically used as a secondary surfactant in personal cleansing compositions based on such primary surfactants. As a secondary surfactant, CAPB provides excellent foam and viscosity building and reduces the irritation potential of alkyl sulfates and alkyl ether sulfates when used in conjunction with them.

However, the inventors have found that increasing the content of CAPB relative to the primary surfactant has been found to impair the delivery of benefit agents from the composition. Benefit agents such as silicones are frequently included in personal cleansing compositions in the form of dispersed emulsion droplets. The effective delivery of such materials to the skin and/or the hair is often a key driver of product performance, especially in compositions such as liquid soaps, body washes and shampoos.

Various types of hair treatment compositions are known where a combination of anionic and zwitterionic surfactants are employed:

US2013/150338 discloses an anti-dandruff shampoo comprising: a) from 0.1 to 5 wt. % of an anti-dandruff zinc salt; b) from 1 to 8 wt. % of an alkyl glycinate and/or alkyl carboxyglycinate; c) from 2 to 16 wt. % of an alkyl sulphate and/or and ethoxylated alkyl sulfate anionic surfactant; and, d) from 1 to 10 wt. % of a fatty acyl isethionate product which product comprises 40 to 80 wt. % fatty acyl isethionate and 15 to 50 wt. % free fatty acid and/or fatty acid salt.

WO2012/072424 discloses an anti-dandruff shampoo comprising: —a) from 0.1 to 5 weight percent of an anti-dandruff zinc salt; b) from 1 to 8 weight percent of a branched alkyloyl isethionate; c) from 1 to 10 weight percent of a fatty acyl isethionate product which product comprises 40 to 80 weight percent fatty acyl isethionate and 15 to 50 weight percent free fatty acid and/or fatty acid salt; and, d) from 0.5 to 14 weight percent of a co-surfactant.

US2014/154200 discloses a hair composition comprising a non-cellulosic polysaccharide derivative: i) having a mean average molecular weight (Mw) from about 100,000 g/mol to about 2,000,000 g/mol; and ii) containing at least one cationic group, with a cationic degree of substitution from about 0.20 to about 0.30. Also a method for providing conditioning effects to the hair, care to hair and/or scalp or a nice dry hair appearance.

US2009/197791 discloses a composition for the treatment or modification of surfaces, comprising: a carrier, a copolymer comprising zwitterionic units A and other units B, the units A comprising a betaine group, which is a sulfobetaine or phosphobetaine group; and the units B which are cationic or potentially cationic units; optionally a surfactant, which may be anionic or amphoteric optionally a salt, an acid and/or a base, and optionally an agent for the treatment or modification of the surface.

EP1433464 discloses a hair cleansing composition comprising an amphipathic amide lipid, an anionic surfactant, and a silicone. Exemplified shampoo compositions purportedly provide hair with good smoothness and moist feeling after use and prevent split ends or hair breakage.

Silicone-containing hair treatment compositions are also known:

WO 17/097817 (Clariant) discloses a shampoo composition comprising an oligoester ammonium salt for the delivery or enhancement of multiple benefits, namely hair detangling, improved wet and dry combing, shine such as hair gloss without the need for silicone, conditioning, hair surface smoothening, hair repair, water resistance, film-forming properties, static charge reduction, anti-frizz, volume, thickening and surfactant activity.

Examples include shampoos containing from 10 to 16 wt % of sodium laureth sulfate, in combination with cocobetaine and a silicone.

US 2006/024381 (P&G) discloses a composition comprising particulate zinc material for the treatment of microbial and fungal infections on the skin and scalp. Examples include shampoo formulations comprising high levels of sodium laureth sulfate in combination with cocamidopropyl betaine and dimethicone.

US 2006/024256 (P&G) discloses a shampoo composition comprising: a) 5 wt % to 50 wt % of one or more detersive surfactants; b) a dispersed gel network phase comprising: i) at least about 0.05 wt % of one or more fatty amphiphiles; ii) at least about 0.01 wt % of one or more secondary surfactants; and iii) water; and c) at least about 20 wt % of an aqueous carrier. Examples include shampoo formulations comprising high levels of sodium laureth sulfate in combination with cocamidopropyl betaine and dimethicone.

WO 98/31327 (P&G) discloses a personal cleansing composition, for the provision of cleaning in combination with improved lathering and conditioning benefits, in the form of a stable aqueous emulsion, comprising: a) 4-50 wt % of a surfactant system; b) >0.1 wt %-<1.0 wt % of a nonionic or anionic water soluble polymer; c) 0.1-5 wt % of a phase separation initiator selected from the group consisting of electrolytes, amphophiles, and mixtures thereof; and d) 50-95 wt % water, wherein said polymer forms visually distinct aqueous droplets in the aqueous surfactant system. Examples include formulations comprising high levels of sodium laureth sulfate in combination with cocamidopropyl betaine and dimethicone.

WO 99/53889 (Unilever) discloses an aqueous shampoo comprising water, at least one cleansing surfactant, a cationic deposition polymer, an emulsified silicone and a microemulsified silicone, which delivers significantly improved conditioning performance. Shampoo compositions with sodium lauryl ether sulphate 2EO (8-12 wt %), cocamidopropyl betaine and a silicone emulsion blend are exemplified.

Further shampoo compositions comprising sodium lauryl ether sulphate 2EO (14 wt %), cocamidopropyl betaine and silicone are disclosed in WO 99/29286 and WO 98/05296 (both Unilever).

Current shampoo products tend to be effective at either cleansing or at delivering scalp mildness. We have found that simply lowering the surfactant concentration, to improve mildness, results in a product that is thin, unstable, and delivers reduced cleaning benefits. Alternative routes for mildness include increasing the ethoxylation of the primary surfactant (commonly SLES) or substitution of milder surfactants for harsher ones, both of which result in a less efficient cleaning performance. Performance benefits such as viscosity, foaming and the delivery of dry lubrication are also negatively affected and the addition of other ingredients is normally required to fix these performance problems. For example, the use of very high salt concentrations, or the introduction of polymeric additives, which negatively impact processing times and sensory performance.

There remains, therefore, a need for shampoo formulations that are capable of improved sebum removal from hair, whilst being mild to scalp skin and hair lipids, without compromising the rheological and foaming properties of the composition or the delivery of silicone or other benefits such as smooth, soft feeling hair.

We have now found that a shampoo composition having a combination of anionic and amphoteric surfactants at enriched amphoteric ratios, reduced surfactant concentrations and specific average SLES ethoxylation levels, gives excellent cleaning, deposition of benefit agents and desirable rheological and foaming characteristics, whilst maintaining mildness to skin and hair lipids and leaving hair feeling smooth and soft.

SUMMARY OF THE INVENTION

In a first aspect the present invention provides a personal cleansing comprising, in an aqueous continuous phase:
(i) from 3 wt % to less than 7 wt %, by weight of the total composition at 100% activity, of an alkyl ether sulfate anionic surfactant of general formula (I):

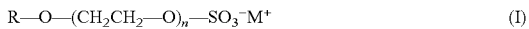

in which R is selected from linear or branched alkyl groups having from 10 to 14 carbon atoms and mixtures thereof; n is a number that represents the average degree of ethoxylation and ranges from 1.5 to 2.5; and M is a solubilizing cation;
(ii) a betaine surfactant selected from an amido betaine amphoteric surfactant of general formula (II):

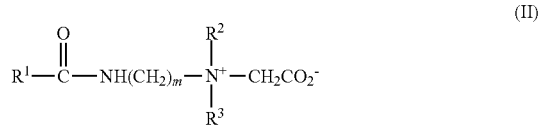

where m is 2 or 3; $R^1C(O)$ is selected from linear or branched, saturated or unsaturated acyl groups having from 8 to 22 carbon atoms and mixtures thereof; and $R^2$ and $R^3$ are each independently selected from alkyl, hydroxyalkyl or carboxyalkyl groups having from 1 to 6 carbon atoms and mixtures thereof; an alkyl betaine of general formula (III):

wherein R is a coco chain,
and mixtures thereof; and
(iii) one or more dispersed benefit agents selected from emulsified silicones with a mean diameter (D3,2) of 4 micrometres or less
in which the weight ratio of (i) to (ii) ranges from 1 to 1 to 4.5:1 and the pH of the composition is from 3 to 6.5; and
the combined amount of (i) and (ii) ranges from 5 wt % to 9 wt % (by weight based on the total weight of the composition);
and wherein the composition further comprises an inorganic electrolyte.

In a second aspect, the invention provides a method of treating hair comprising the step of applying to the hair a composition as defined by the first aspect.

Preferably the method comprises an additional step of massaging the composition of the first invention into the hair and scalp.

Preferably the method comprises an additional step of rinsing the hair.

DETAILED DESCRIPTION OF THE INVENTION

All molecular weights as used herein are weight average molecular weights, unless otherwise specified.

Aqueous Continuous Phase

By "aqueous continuous phase" is meant a continuous phase which has water as its basis.

Suitably, the composition of the invention will comprise from about 75 to about 95%, preferably from 85 to 95%, more preferably from 90 to 95% water (by weight based on the total weight of the composition).

The Alkyl Ether Sulfate Anionic Surfactant

The composition of the invention comprises (i) one or more alkyl ether sulfate anionic surfactants of general formula (I)

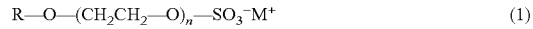

in which R is selected from linear or branched alkyl groups having from 10 to 14 carbon atoms and mixtures thereof; n is a number that represents the average degree of ethoxylation and ranges from 1.5 to 2.5; and M is a solubilizing cation.

Preferably R in general formula (I) is a $C_{10}$ or $C_{12}$ linear alkyl group.

Preferably M in general formula (I) is selected from alkali metal cations (such as sodium or potassium), ammonium cations and substituted ammonium cations (such as alkylammonium, alkanolammonium or glucammonium).

Commercially produced alkyl ether sulfate anionic surfactants of general formula (I) may be made by sulfating fatty alcohol ethoxylates formed by reaction of ethylene oxide with fatty alcohol of formula R—OH (where R is as defined above). The reaction of the fatty alcohol with ethylene oxide typically yields mixtures of homologues which are alcohol polyethylene glycol ethers. Unreacted fatty alcohol may also be present in the mixture.

The distribution curve of the homologue mixture normally shows a maximum in the range from n−3 to n+3, where n denotes the average degree of ethoxylation in general formula (I). The value of n in general formula may be an integer or fraction, and may governed by factors such as the starting molar ratio of ethylene oxide to fatty alcohol in the reaction mixture, and the temperature, time and catalytic conditions under which the reaction takes place. Average n ranges from 1.5 to 2.5, preferably from 1.7 to 2.3, most preferably from 1.8 to 2.2. Blends of materials having different ethoxylation levels can be used to achieve an average degree of ethoxylation within the range.

Particularly preferred is SLES with an average of 2EO (i.e. sodium lauryl ether sulfate in which the average degree of ethoxylation n is 2.0). A suitable example of such a material is TEXAPON® N 70 (ex BASF). A further example is sodium pareth ether sulphate, preferably with an average of 2EO.

All amounts referred to herein are based on 100% activity unless otherwise stated.

All amounts referred to herein are based on 100% activity (or "active") unless otherwise stated. By 100% activity (or "active") is meant that the material is not diluted and is at 100% v/v or wt/wt. Many materials used in personal care formulations are commercially available at different active concentrations, for example at 70% active or 60% active. For example, 100 ml of 70% active surfactant provides the same amount of active material as 70 ml of 100% active surfactant. Therefore, in order to provide for variations in activities of materials, all amounts are based on 100% active materials.

The aqueous continuous phase comprises a total amount of anionic, amphoteric and zwitterionic surfactant consisting of (i) and (ii) below. That is to say, no further anionic, amphoteric and zwitterionic surfactants are present in the compositions of the invention. Preferably, no other surfactants, for example, nonionic surfactants are present in the compositions of the invention.

The amount of alkyl ether sulfate anionic surfactant, at 100% activity, of general formula (I) ranges from 3 to less than 7% (for example from 3 to 6.99%), preferably 3 to 6.9%, more preferably from 3 to 6.5%, still more preferably from 3 to 6%, even more preferably from 3 to 5% and most preferably from 3.25 to 5% (by weight based on the total weight of the composition).

In a particularly preferred composition according to the invention the alkyl ether sulfate anionic surfactant of general formula (I) is SLES 2EO (i.e. sodium lauryl ether sulfate in which the average degree of ethoxylation n is 2.0), in an amount ranging from 3 to less than 7%, more preferably from 3 to 6.5 (by weight based on the total weight of the composition).

Amido Betaine CAPB

The composition of the invention comprises (ii) a betaine surfactant selected from an amido betaine amphoteric surfactant of general formula (II):

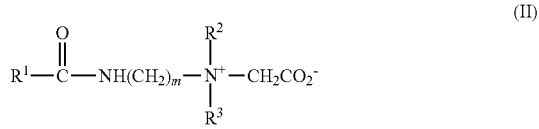

(II)

where m is 2 or 3; $R^1C(O)$ is selected from linear or branched, saturated or unsaturated acyl groups having from 8 to 22 carbon atoms and mixtures thereof; and $R^2$ and $R^3$ are each independently selected from alkyl, hydroxyalkyl or carboxyalkyl groups having from 1 to 6 carbon atoms and mixtures thereof;

an alkyl betaine of general formula (III):

(III)

wherein R is a cocoyl group, and mixtures thereof.

Amido betaines have a zwitterionic structure which makes them amphoteric.

Preferably, $R^1C(O)$ in general formula (II) is selected from linear acyl groups having from $C_8$ to $C_{18}$ carbon atoms and 0, 1, 2 or 3 double bonds and mixtures thereof.

More preferably, $R^1C(O)$ in general formula (II) is selected from lauroyl, myristoyl, palmitoyl, stearoyl, oleoyl and cocoyl groups and mixtures thereof. Most preferably $R^1C(O)$ in general formula (II) is a cocoyl group.

Preferably $R^2$ and $R^3$ in general formula (II) are both methyl.

Mixtures of any of the above described materials may also be used.

The amount of amido betaine amphoteric surfactants of general formula (II) and (III) preferably ranges from 1 to 3.5 wt %, more preferably from 1 to 3 wt %, most preferably from 1.5 to 2.5 wt % (based on the total weight of the composition).

In a preferred composition according to the invention the amido betaine amphoteric surfactant of general formula (II) is cocamidopropylbetaine, in an amount ranging from 1 to 3% (by weight based on the total weight of the composition).

R in general formula (III) is a cocoyl group. This is preferably a blend of carbon chains resulting in an average carbon chain length of 12.

The combined amount of (i) and (ii) ranges from 5 to 10 wt %, preferably from 5 to 9 wt % (based on the total weight of the composition).

Preferably the weight ratio of the alkyl ether sulfate anionic surfactant (i) to the amido betaine amphoteric surfactant (ii) ranges from 1:1 to 4:1 [4.5:1?], more preferably from 1.5:1 to 3.75:1 and most preferably 2:1 to 3.5:1.

An especially preferred composition according to the invention comprises (i) SLES 2EO in an amount ranging from 3 to less than 7 wt % (by weight based on the total weight of the composition and 100% active material); and (ii) cocamidopropylbetaine in an amount ranging from 1 to 3 wt % (by weight based on the total weight of the composition and 100% active material).

The PH

The pH of the composition of the invention ranges from 3 to 6.5, preferably from 3 to 5.1, more preferably from 3.5 to 5.

Benefit Agents—Emulsified Silicones

The composition of the invention comprises (iii) one or more dispersed benefit agents selected from emulsified silicones with a mean diameter (D3,2) of 4 micrometres or less;

The term "benefit agent" in the context of this invention includes materials which can provide a benefit to the hair and/or the scalp and/or the skin (preferably the hair and/or the scalp).

Emulsified silicones for inclusion in the composition of the invention typically have a mean droplet diameter (D3,2) of 4 micrometres or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

Suitable silicones for use in the invention include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Such silicones are preferably non-volatile (with vapour pressure of less than 1000 Pa at 25° C.), and preferably have a molecular weight of greater than 100,000, more preferably greater than 250,000.

Such silicones preferably have a kinematic viscosity of greater than 50,000 cS ($mm^2 \cdot s^{-1}$) and more preferably a kinematic viscosity of greater than 500,000 cS ($mm^2 \cdot s^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a mean droplet diameter (D3,2) of less than 0.15 micrometres are generally termed microemulsions.

Examples of suitable pre-formed silicone emulsions include emulsions DC2-1766, DC2-1784, DC-1785, DC-1786, DC-1788, DC-1310, DC-7123, DC-7051 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

In preferred compositions according to the invention, the amount of emulsified silicone (per se as active ingredient) ranges from 0.1 to 4%, more preferably from 0.5 to 2% (by weight based on the total weight of the composition).

Cationic Polymers

Preferably, the composition of the invention further comprises one or more cationic polymers. Such polymers may enhance the delivery of conditioning agents and thereby improve the conditioning benefits obtained.

Cationic polymers for use in the invention suitably have a cationic charge density ranging from about 0.3 to about 4 meq/g, preferably from about 0.4 to about 3.5 meq/g. The term "cationic charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain. Cationic charge density can be determined according to the Kjeldahl Method. Those skilled in the art will recognize that the charge density of amino-containing polymers may vary depending upon pH and the isoelectric point of the amino groups. The charge density should be within the above limits at the pH of intended use.

Suitable cationic polymers for use in the invention include cationic polysaccharide derivatives, such as cationic cellulose derivatives, cationic starch derivatives, and cationic guar gum derivatives.

Preferred cationic polysaccharide derivatives for use in the invention include cationic guar gum derivatives and cationic cellulose derivatives.

Examples of preferred cationic guar gum derivatives for use in the invention include guar hydroxypropyltrimethylammonium chlorides. Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Guar hydroxypropyltrimethylammonium chlorides for use in the invention generally have an average molecular weight (weight average molecular mass ($M_w$) determined by size exclusion chromatography) in the range 500,000 to 3 million g/mol, more preferably 800,000 to 2.5 million g/mol.

Guar hydroxypropyltrimethylammonium chlorides for use in the invention (preferably guar hydroxypropyltrimethylammonium chlorides) generally have a charge density ranging from 0.5 to 1.8 meq/g.

Examples of preferred cationic cellulose derivatives for use in the invention include poly(1,2-oxyethanediyl)-2-hydroxy-3-trimethylammonium propyl chloride cellulose ethers (INCI: Polyquaternium-10).

Mixtures of any of the above described cationic polymers may also be used.

In a typical composition according to the invention the amount of cationic polymer will generally range from 0.05 to 0.5%, and preferably ranges from 0.15 to 0.2% by weight based on the total weight of the composition.

In a preferred composition according to the invention the one or more cationic polymers are selected from guar hydroxypropyltrimethylammonium chlorides having a $M_w$ ranging from 800,000 to 2.5 million g/mol and a charge density ranging from 0.5 to 1.8 meq/g; in an amount ranging from 0.15 to 0.2% (by weight based on the total weight of the composition).

Structurants

Preferably, the composition of the invention further comprises one or more structurants to assist in the suspension of dispersed benefit agent and provide phase. Suitable structurants include polyacrylic acids, polymethacrylic acids, cross-linked polymers of acrylic acid, cross-linked polymers of methacrylic acid, copolymers of acrylic acid with a hydrophobic monomer, copolymers of methacrylic acid with a hydrophobic monomer, copolymers of carboxylic acid-containing monomers and acrylic esters, copolymers of carboxylic acid-containing monomers and methacrylic esters, cross-linked copolymers of acrylic acid and acrylate esters, cross-linked copolymers of methacrylic acid and acrylate esters heteropolysaccharide gums and crystalline long chain acyl derivatives.

Preferred structurants are selected from polyacrylic acids, polymethacrylic acids, cross-linked polymers of acrylic acid, cross-linked polymers of methacrylic acid and mixtures thereof.

Mixtures of any of the above structurants may be used.

When included, the total amount of structurant is generally 0.1 to 10%, preferably from 0.1 to 3%, more preferably from 0.2 to 2%, most preferably from 0.3 to 0.9% (by weight based on the total weight of the composition).

A preferred composition comprises a structurant selected from polyacrylic acids, polymethacrylic acids, cross-linked polymers of acrylic acid, cross-linked polymers of methacrylic acid and mixtures thereof in an amount of from 0.1 to 10%, preferably from 0.1 to 3%, more preferably from 0.2 to 2%, most preferably from 0.3 to 0.9% (by weight based on the total weight of the composition).

Inorganic Electrolyte—Viscosity

We have found that, surprisingly, the compositions of the invention are amenable to building viscosity very well. It is thus possible to build viscosity at lower concentrations at 2EO better than at conventional non-amphoteric-enriched ratios at 1 EO. This is further advantage of the invention.

The composition of the invention includes at least one inorganic electrolyte. The inorganic electrolyte may be used to help provide viscosity to the composition.

The viscosity of the composition suitably ranges from 2,500 to 20,000 mPa·s, preferably from 3,000 to 15,000 mPa·s, more preferably from 4,000 to 12,000 mPa·s when measured using a Brookfield V2 viscometer (spindle RTV5, 1 minute, 20 rpm) at 30° C.

At these range our products are pourable yet thick enough to satisfy the consumer desire for thick compositions.

Suitable inorganic electrolytes include metal chlorides (such as sodium chloride, potassium chloride, calcium chloride, magnesium chloride, zinc chloride, ferric chloride and aluminium chloride) and metal sulfates (such as sodium sulfate and magnesium sulfate).

It is intended that the inorganic electrolyte is separate from any inorganic electrolytes that may be present in the raw materials of the invention.

Examples of preferred inorganic electrolytes for use in the invention include sodium chloride, potassium chloride, magnesium sulfate and mixtures thereof.

Mixtures of any of the above described materials may also be suitable.

The amount of inorganic electrolyte in compositions of the invention generally ranges from 0.5 to 25%, preferably from 0.75 to 15%, more preferably from 1 to 5%, most preferably from 1 to 3% (by weight based on the total weight of the composition).

A Preservative

A personal cleansing composition preferably comprises one or more preservatives, selected from sodium benzoate, sodium salicylate, benzyl alcohol, phenoxyethanol, 1,2-alkanediols, Iodopropynyl butylcarbamate (IPBC), 5-chloro-2-methyl-2H-isothiazol-3-one, 2-methyl-2H-isothiazol-3-one, or mixtures thereof. The most preferred preservative is sodium benzoate.

A preferred composition has a pH of from 3 to 5.1 and comprises a preservative that is sodium benzoate.

Preferably, the compositions of the invention are free from anti-dandruff actives, most preferably free from zinc pyrithione. In the context of the invention, by free from is meant having less than 0.4 weight %, more preferably less than 0.1 weight %, even more preferably less than 0.05 weight %, still more preferably less than 0.001 weight %, yet preferably less than 0.0001 weight %, and most preferably 0 weight % of antidandruff active by weight of the total composition.

Further Optional Ingredients

A composition of the invention may contain further optional ingredients to enhance performance and/or consumer acceptability. Examples of such ingredients include fragrance, dyes and pigments, pH adjusting agents and preservatives or antimicrobials. Each of these ingredients will be present in an amount effective to accomplish its purpose. Generally, these optional ingredients are included individually at an amount of up to 5% (by weight based on the total weight of the composition).

The composition of the invention is primarily intended for topical application to the body, preferably the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples.

Example

Rinse-off aqueous hair cleansing shampoo formulations were prepared, having ingredients as shown in the tables below.

All shampoos were prepared using the following method:
1. A vessel was charged with water. Surfactants and any structurant were added with stirring.
2. The mixture was heated to 30° C. and mixed until completely homogenous.
3. Any cationic polymer and silicone emulsion was then added and mixed well.
4. Any preservative and perfume was added.
5. The pH was adjusted to pH 4.5 using citric acid.
6. Salt was then added to adjust the viscosity.

The following characterisation methods were used:

Viscosity Measurement:

The viscosities of the compositions in these examples were measured using a Brookfield V2 viscometer (spindle RTV5, 1 minute, 20 rpm) at 30° C.

Foam Properties:

Foam volume was measured using the following method:—

An oily soil (0.02 g) and shampoo (2 g) were added to a 250 ml measuring cylinder and made up to 20 g total with water.

The liquid was swirled (5 sec) to start the mixing of the shampoo.

The cylinder was inverted 10 times (in a steady, reproducible movement) and left for 30 s before the foam height was recorded (Flash Foam Reading).

The cylinder was then shaken 20 more times, left for 30 s and the foam height recorded.

Finally, the cylinder was shaken 30 more times, left for 30 s and the foam level recorded (Foam Volume Reading).

This was repeated three times for each shampoo formula and the average and standard deviation for each point calculated.

Silicone Deposition:

Virgin hair switches were treated with the compositions as follows:

Hair was washed using the compositions of these examples using the following method:—

The hair switches were held under running water for 30 seconds, the composition applied at a dose of 0.1 ml of composition per 1 g of hair and rubbed into the hair for 30 seconds. Excess lather was removed by holding under running water for 30 seconds and the composition application repeated. The hair was rinsed under running water for 30 seconds.

Switches were dried before the level of silicone was quantified using x-ray fluorescence (XRF).

Mildness to Protein

A colour test was used to measure the level of damage to Zein protein, which had been treated with blue dye, when contacted with a shampoo composition. The protein was soaked in a 10% aqueous solution of the test composition for 10 min. The level of damage was indicated by the amount of blue dye released. The darker the dye, the harsher the composition.

Cleaning Efficiency

The compositions were tested for ability to clean oily (hydrophobic) soils containing a brominated oil marker. Hair switches were prepared by first treating with a known concentration of an oily soil with Brominated marker. The 'pre-soiled' switches were washed by treating with the test composition (0.1 ml of test product per g of hair), 30 second application and 30 second rinse. The switches were dried and the level of brominated marker remaining on the hair was determined by XRF and used to calculate the cleaning efficiency of the test composition.

Shampoos 1a, 1b an 1c are illustrative examples, demonstrating the effect of reducing the concentration.

Examples 3b, 3d, 3f and 4b represent formulations according to the invention.

Examples 3a, 3c, 3e and 4a are comparative examples.

Example 1: General Effect on Viscosity of Reducing Surfactant Concentration; Shampoos 1a, 1b and 1c It is known that reducing the surfactant concentration of shampoo improves mildness but also directly affects viscosity. This is illustrated by the following Example.

Shampoos 1a, 1b and 1c with surfactant concentrations of 13.6, 10.2 and 6.8 wt % were prepared as above and the viscosity of each composition measured.

TABLE 1

Amount (wt %) of ingredients in Shampoos 1a, 1b and 1c

| Ingredient (INCI and/or Trade Name) | % active | 1a | 1b | 1c |
|---|---|---|---|---|
| Sodium Lauyl Ether Sulfate (1EO)/Texapon N701 (SLES) | 70 | 17.14 | 12.86 | 8.57 |
| Cocamidopropyl betaine/Tego betain CK KB5 (CAPB) | 30 | 5.33 | 4 | 2.67 |
| Guar Hydroxypropyltrimonium Chloride | 100 | 0.2 | 0.2 | 0.2 |
| Sodium Benzoate | 100 | 0.5 | 0.5 | 0.5 |
| Disodium Ethylenediaminetetraacetic acid | 100 | 0.05 | 0.05 | 0.05 |
| Citric acid | 100 | to pH 4.5 | to pH 4.5 | to pH 4.5 |
| Sodium Chloride | 100 | 3 | 3 | 3 |
| Carbomer | 100 | 0.4 | 0.4 | 0.4 |
| Perfume | 100 | 0.5 | 0.5 | 0.5 |
| Dimethiconol/TEA-dodecylbenzene sulfonate | 50 | 2 | 2 | 2 |
| Water | 100 | to 100% | to 100% | to 100% |
| Surfactant ratio (SLES:CAPB); at 100% active | | 7.5:1 | 7.5:1 | 7.5:1 |

TABLE 2

Viscosities of Shampoos 1a, 1b and 1c.

| | Concentration (wt %) of surfactant (at 100% active) | Viscosity (cP) |
|---|---|---|
| 1a | 13.6% | 24,750 |
| 1b | 10.2% | 12,100 |
| 1c | 6.8% | 2,700 |

It will be seen that, as the concentration of surfactant decreases, the viscosity is reduced and the products become unacceptably thin.

Example 2: Effect of EQ Level on Foam Volume and Silicone Deposition: Shampoos 3a, 3b, 3c, 3d, 3e and 3f Shampoo compositions, 3a to 3f having a level of ethoxylation ranging from 1 EO to 3EO were prepared. The compositions of 3a and 3b are given in Table 3.

TABLE 3

Amount (wt %) of ingredients in Shampoos 3a-3f

| INCI and/or Trade Name | Activity (%) | 3a | 3b | 3c | 3d | 3e | 3f |
|---|---|---|---|---|---|---|---|
| Sodium Lauyl Ether Sulfate (1EO)/Texapon N701 | 70 | 4.86 | — | 9.57 | | | 4.79 |
| Sodium Lauyl Ether Sulfate (2EO)/Texapon N70 | 70 | — | 4.86 | | 9.57 | | |
| Sodium Lauyl Ether Sulfate (3EO)/Texapon N703 GT | 70 | | | | | 9.57 | 4.79 |
| Cocamidopropyl betaine/Tego betain CK KB5 | 30 | 5.33 | 5.33 | 11.00 | 11.00 | 11.00 | 11.00 |

TABLE 3-continued

Amount (wt %) of ingredients in Shampoos 3a-3f

| INCI and/or Trade Name | Activity (%) | 3a | 3b | 3c | 3d | 3e | 3f |
|---|---|---|---|---|---|---|---|
| Guar Hydroxypropyl-trimonium Chloride | 100 | 0.2 | 0.2 | 0.2 | 0.2 | 0.2 | 0.2 |
| Sodium Benzoate | 100 | 0.5 | 0.5 | 0.5 | 0.5 | 0.5 | 0.5 |
| Disodium Ethylene-diaminetetraacetic acid | 100 | 0.05 | 0.05 | 0.05 | 0.05 | 0.05 | 0.05 |
| Citric acid | 100 | to pH 4.5 | to pH 4.5 | to pH 4.5 | to pH 4.5 | to pH 4.5 | to pH 4.5 |
| Sodium Chloride | 100 | 3 | 3 | 0 | 0.13 | 0.86 | 0.17 |
| Carbomer | 100 | 0.4 | 0.4 | 0.4 | 0.4 | 0.4 | 0.4 |
| Perfume | 100 | 0.5 | 0.5 | 0.5 | 0.5 | 0.5 | 0.5 |
| Dimethiconol/TEA-dodecylbenzene sulfonate | 50 | 2 | 2 | 2 | 2 | 2 | 2 |
| Water | 100 | to 100 | to 100 | to 100 | to 100 | to 100 | to 100 |
| Surfactant ratio (SLES:CAPB); at 100% active | | 2.1:1 | 2.1:1 | 2:1 | 2:1 | 2:1 | 2:1 |

The foam volume and silicone deposition of these formulations were then tested, and the results shown in Tables 4 and 5.

TABLE 4

Foam volume and silicone deposition of Shampoos 3a and 3b

| | Ethoxylation level | Foam Volume, ml | Silicone Deposition, ppm |
|---|---|---|---|
| 3a | 1EO | 69 | 14 |
| 3b | 2EO | 103 | 362 |

Surprisingly, the use of a surfactant having an average ethoxylation of 2EO results in dramatically higher foam volume and silicone deposition that the corresponding 1 EO surfactant.

TABLE 5

Silicone deposition on hair treated with Shampoos 3c to 3f

| | Ethoxylation level | Silicone Deposition, ppm |
|---|---|---|
| 3c | 1EO | 125 |
| 3d | 2EO | 327 |
| 3e | 3EO | 78 |
| 3f | 1EO + 3EO blend = 2EO ave. | 236 |

It will be seen that foam and silicone deposition are greatly improved by using a level of ethoxylation of an average of 2 EO.

Moreover, a 1+3EO blend (average 2EO), provides a synergistic effect on silicone deposition compared to 3EO and 1 EO alone.

Example 3: Mildness of Shampoos 4a and 4b

A composition in accordance with the invention was tested for mildness to protein, (4b) versus a comparative product (4a).

Shampoo compositions, 4a and 4b having a level of ethoxylation of 1 EO and 2EO respectively were prepared. The compositions of 4a and 4b are given in Table 6.

TABLE 6

Amount (wt %) of ingredients in Shampoos 4a and 4b

| INCI and/or Trade Name | % active | 4a | 4b |
|---|---|---|---|
| Sodium Lauyl Ether Sulfate (1EO)/Texapon N701 | 70 | 17.14 | |
| Sodium Lauyl Ether Sulfate (2EO)/Texapon N70 | 70 | | 4.86 |
| Cocamidopropyl betaine/Tego betain CK KB5 | 30 | 5.33 | 5.33 |
| Guar Hydroxypropyl-trimonium Chloride | 100 | 0.2 | 0.2 |
| Sodium Benzoate | 100 | 0.5 | 0.5 |
| Disodium Ethylene-diaminetetraacetic acid | 100 | 0.05 | 0.05 |
| Citric acid | 100 | to pH 4.5 | to pH 4.5 |
| Sodium Chloride | 100 | 2 | 3 |
| Carbomer | 100 | 0.4 | 0.4 |
| Perfume | 100 | 0.5 | 0.5 |
| Dimethiconol/TEA-dodecylbenzene sulfonate | 50 | 2 | 2 |
| Water | 100 | to 100% | to 100% |
| Surfactant ratio (SLES:CAPB); at 100% active | | 7.5:1 | 2.1:1 |

The mildness of formulations 4a and 4b were tested using the Zein protein method and the results shown in Table 7.

TABLE 7 mildness to protein of shampoos 4a and 4b

| | Ethoxylation level | Mildness to Protein (blue dye release) (b*) |
|---|---|---|
| 4a | 1EO | −10.5 |
| 4b | 2EO | −1.3 |

It is clear that the shampoo in accordance with the invention (4b) has enhanced mildness to protein versus the comparative composition (4a).

Example 4: Cleaning Efficiency of Shampoos 4a and 3c-3f

Compositions in accordance with the invention (3d and 3f) were tested for cleaning efficiency, using a brominated oil soil as described above, versus comparative compositions 3c, 3e and 4a.

TABLE 8

Cleaning efficiency of shampoos 4a and 3c-3f

|  | Ethoxylation level/total surfactant concentration/ SLES:CAPB ratio | Silicone Deposition, ppm | Cleaning Efficiency, % (oily soil) |
|---|---|---|---|
| 4a | 1EO/13.6%/7.5:1 | 280 | 87 |
| 3c | 1EO/10%/2:1 | 125 | 95 |
| 3d | 2EO/10%, 2:1 | 327 | 94 |
| 3e | 3EO/10%, 2:1 | 78 | 96 |
| 3f | 1EO + 3EO/10%/2:1 | 236 | 94 |

The results show that the compositions in accordance with the invention offer excellent cleaning efficiency, without compromising the level of deposition of silicone. In particular, despite the higher level of surfactant, 4a has a relatively poor cleansing efficiency.

The invention claimed is:

1. A personal cleansing composition comprising:
   (A) a total amount of anionic surfactant, amphoteric surfactant and zwitterionic surfactant consisting of:
      (i) from 3 wt % to less than 7 wt %, by weight of the total composition at 100% activity, of an alkyl ether sulfate anionic surfactant of general formula (I):

$$R\text{—}O\text{—}(CH_2CH_2\text{—}O)_n\text{—}SO_3^-M^+ \quad (I)$$

wherein R is selected from linear or branched alkyl groups having from 10 to 14 carbon atoms and mixtures thereof; n is a number that represents the average degree of ethoxylation and ranges from 1.5 to 2.5; and M is a solubilizing cation; and
      (ii) an amphoteric or zwitterionic surfactant, selected from the group consisting of:
   a betaine surfactant selected from an amido betaine amphoteric surfactant of general formula (II):

$$R^1\text{—}\underset{\|}{\overset{O}{C}}\text{—}NH(CH_2)_m\text{—}\underset{R^3}{\overset{R^2}{N^+}}\text{—}CH_2CO_2^- \quad (II)$$

where m is 2 or 3; $R^1C(O)$ is selected from linear or branched, saturated or unsaturated acyl groups having from 8 to 22 carbon atoms and mixtures thereof; and $R^2$ and $R^3$ are each independently selected from alkyl, hydroxyalkyl or carboxyalkyl groups having from 1 to 6 carbon atoms and mixtures thereof; and an alkyl betaine of general formula (III):

$$R\text{—}\underset{CH_3}{\overset{CH_3}{N^+}}\text{—}\overset{H_2}{C}\text{—}\underset{\|}{\overset{O}{C}}\text{—}O^- \quad (III)$$

wherein R is a coco chain, and mixtures thereof;
   (B) one or more dispersed benefit agents selected from emulsified silicones with a mean diameter (D3,2) of 4 micrometres or less;
   (C) an inorganic electrolyte;
   wherein
      the composition is free of other surfactants:
      the weight ratio of (i) to (ii) ranges from 1:1 to 4.5:1 and the pH of the composition is from 3 to 6.5; and
      the combined amount of (i) and (ii) ranges from 5 wt % to 9 wt % by weight based on the total weight of the composition;
   and wherein the composition has a viscosity from about 4,000 to about 12,000 mPa·s when measured using a Brookfield V2 viscometer with spindle RTV5 for 1 minute at 20 rpm and 30° C.

2. The composition according to claim 1, wherein the alkyl ether sulfate anionic surfactant of general formula (I) is sodium lauryl ether sulfate with an average degree of ethoxylation of 2, in an amount ranging from 3 to 6% by weight based on the total weight of the composition and at 100% activity.

3. The composition according to claim 1, wherein the amido betaine amphoteric surfactant of general formula (II) is cocamidopropylbetaine, in an amount ranging from 1 to 3.5% by weight based on the total weight of the composition.

4. The composition according to claim 1, wherein the weight ratio of (i) to (ii) ranges from 1.5:1 to 4:1.

5. The composition according to claim 1, wherein the amount of emulsified silicone (per se as active ingredient) ranges from 0.1 to 4% by weight based on the total weight of the composition.

6. The composition according to claim 1, comprising from 0.25 to 25 wt % of an inorganic electrolyte based on total weight of the composition, wherein the inorganic electrolyte is selected from the group consisting of sodium chloride, potassium chloride, calcium chloride, magnesium chloride, zinc chloride, ferric chloride and aluminium chloride, sodium sulfate, magnesium sulfate and mixtures thereof.

7. The composition according to claim 1, further comprising one or more structurants selected from polyacrylic acids, polymethacrylic acids, cross-linked polymers of acrylic acid, cross-linked polymers of methacrylic acid and mixtures thereof.

8. The composition according to claim 7, wherein the structurant is present in an amount of 0.1 to 3 wt %.

9. The composition according to claim 1, further comprising one or more preservatives selected from sodium benzoate, sodium salicylate, benzyl alcohol, phenoxyethanol, 1,2-alkanediols, iodopropynyl butylcarbamate (IPBC), 5-chloro-2-methyl-2H-isothiazol-3-one, 2-methyl-2H-isothiazol-3-one, or mixtures thereof.

10. The composition according to claim 1, further comprising one or more cationic polymers selected from guar hydroxypropyltrimethylammonium chlorides having a Mw ranging from 800,000 to 2.5 million g/mol and a charge density ranging from 0.5 to 1.8 meq/g; in an amount ranging from 0.15 to 0.2% by weight based on the total weight of the composition.

11. A method of treating hair comprising the step of applying to the hair the composition of claim 1.

12. The method of claim 11, wherein the method comprises an additional step of massaging the composition into the hair and scalp.

13. The method of claim 12, wherein the method comprises the additional step of rinsing the hair.

14. The composition according to claim 1, which is a shampoo composition.

15. A personal cleansing composition consisting of:
(A) a total amount of anionic surfactant, amphoteric surfactant and zwitterionic surfactant consisting of:
(i) from 3 wt % to less than 7 wt %, by weight of the total composition at 100% activity, of an alkyl ether sulfate anionic surfactant of general formula (I):

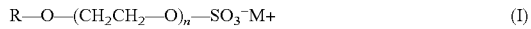

wherein R is selected from linear or branched alkyl groups having from 10 to 14 carbon atoms and mixtures thereof; n is a number that represents the average degree of ethoxylation and ranges from 1.5 to 2.5; and M is a solubilizing cation; and
(ii) 1% to 3.5% by weight of the total composition at 100% activity, of an amphoteric or zwitterionic surfactant, selected from the group consisting of:
a betaine surfactant selected from an amido betaine amphoteric surfactant of general formula (II):

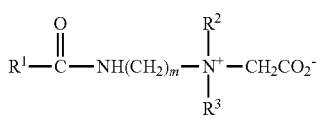

where m is 2 or 3; $R^1C(O)$ is selected from linear or branched, saturated or unsaturated acyl groups having from 8 to 22 carbon atoms and mixtures thereof; and $R^2$ and $R^3$ are each independently selected from alkyl, hydroxyalkyl or carboxyalkyl groups having from 1 to 6 carbon atoms and mixtures thereof;
an alkyl betaine of general formula (III):

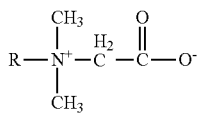

wherein R is a coco chain,
and mixtures thereof;
(B) one or more dispersed benefit agents selected from emulsified silicones with a mean diameter (D3,2) of 4 micrometres or less;
(C) an inorganic electrolyte;
(D) water;
(E) optionally one or more cationic polymers selected from guar hydroxypropyltrimethyl ammonium chlorides;
(F) optionally one or more structurants;
(G) optionally one or more preservatives;
(H) optionally one or more pH adjusting agents; and
(I) optionally an ingredient selected from the group consisting of disodium ethylenediaminetetraacetic acid, fragrance, dyes and pigments;
wherein
the weight ratio of (i) to (ii) ranges from 1:1 to 4.5:1 and the pH of the composition is from 3 to 6.5; and
the combined amount of (i) and (ii) ranges from 5 wt % to 9 wt % by weight based on the total weight of the composition.

16. The composition according to claim 15, wherein the one or more pH adjusting agent is citric acid.

17. A personal cleansing composition for hair, scalp and skin consisting of:
(A) a total amount of anionic surfactant, amphoteric surfactant and zwitterionic surfactant consisting of:
(i) from 3 wt % to 7 wt % by weight of the total composition, at 100% activity, of sodium lauryl ether sulfate with an average degree of ethoxylation of 2; and
(ii) 1% to 3.5% by weight of the total composition at 100% activity of cocamidopropylbetaine;
(B) 0.1 to 4% by weight of an emulsified silicone selected from the group consisting of dimethicones, dimethiconols, and amodimethicones;
(C) 1 wt % to 5 wt % by weight of sodium chloride;
(D) water;
(E) 0.15 wt % to 0.2 wt % of one or more cationic polymer polymers selected from guar hydroxypropyltrimethylammonium chlorides having a Mw ranging from 800,000 to 2.5 million g/mol and a charge density ranging from 0.5 to 1.8 meq/g;
(F) 0.1 to 3 wt % of a structurant selected from the group consisting of polyacrylic acids, polymethacrylic acids, cross-linked polymers of acrylic acid, and cross-linked polymers of methacrylic acid;
(G) optionally a preservative comprising sodium benzoate;
(H) optionally a pH adjusting agent comprising citric acid; and
(I) optionally an ingredient selected from the group consisting of disodium ethylenediaminetetraacetic acid, dye, pigment and a benefit agent;
wherein
the weight ratio of (i) to (ii) ranges from 1:1 to 4.5:1 and the pH of the composition is from 3 to 6.5; and
the combined amount of (i) and (ii) ranges from 5 wt % to 9 wt % by weight based on the total weight of the composition.

18. The composition according to claim 17, wherein the emulsified silicone has a mean diameter (D3,2) of 4 micrometres or less.

* * * * *